(12) United States Patent
Gindilis

(10) Patent No.: US 11,939,629 B2
(45) Date of Patent: Mar. 26, 2024

(54) METHODS AND SYSTEMS THAT DETECT NUCLEIC-ACID TARGETS

(71) Applicant: Andrei Gindilis, Mukilteo, WA (US)

(72) Inventor: Andrei Gindilis, Mukilteo, WA (US)

( * ) Notice: Subject to any disclaimer, the term of this patent is extended or adjusted under 35 U.S.C. 154(b) by 1263 days.

(21) Appl. No.: 16/052,538

(22) Filed: Aug. 1, 2018

(65) Prior Publication Data

US 2019/0185920 A1    Jun. 20, 2019

Related U.S. Application Data

(60) Provisional application No. 62/539,984, filed on Aug. 1, 2017.

(51) Int. Cl.
 *C12P 19/34* (2006.01)
 *C12Q 1/6816* (2018.01)
 *C12Q 1/6823* (2018.01)
 *C12Q 1/6832* (2018.01)
 *C12Q 1/686* (2018.01)

(52) U.S. Cl.
 CPC ......... *C12Q 1/6832* (2013.01); *C12Q 1/6816* (2013.01); *C12Q 1/6823* (2013.01); *C12Q 1/686* (2013.01)

(58) Field of Classification Search
 None
 See application file for complete search history.

(56) References Cited

U.S. PATENT DOCUMENTS 6,326,486 B1 *  12/2001  Hogan ................... C12Q 1/689
                                                    536/24.32
2002/0151040 A1 * 10/2002  O' Keefe ............ B01L 3/50857
                                                    435/287.2

FOREIGN PATENT DOCUMENTS

WO    WO-2016086004 A1 *  6/2016  ........... C12Q 1/6823

OTHER PUBLICATIONS

Forster et al., "A human gut bacterial genome and culture collection for improved metagenomic analyses", Nature Biotechnology, vol. 37, Feb. 2019, pp. 186-192. (Year: 2019).*
Sah et al., "Complete Genome Sequence of a 2019 Novel Coronavirus (SARS-CoV-2) Strain isolated in Nepal", Microbiology Resource Announcements, vol. 9, Issue 11, Mar. 12, 2020, 1-3. (Year: 2020).*
Zeberg et al., "The major genetic risk factor for severe COVID-19 is inherited from Neanderthals", Nature, Sep. 30, 2020, pp. 1-3. (Year: 2020).*

* cited by examiner

*Primary Examiner* — Bradley L. Sisson
(74) *Attorney, Agent, or Firm* — Olympic Patent Works PLLC

(57) ABSTRACT

The current document relates generally to the field of nucleic-acid detection and, in particular, to a highly sensitive and specific nucleic-acid-detection method that includes hybridization of a specific nucleic-acid target to a recognition probe, subsequent specific cleavage of the double-stranded target-probe helix at a specific restriction site, and exponential amplification of the enzymatic cleavage accompanied by release of a molecular marker.

14 Claims, 12 Drawing Sheets

Specification includes a Sequence Listing.

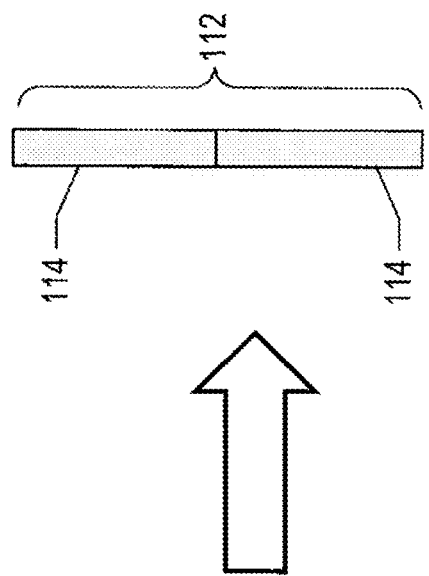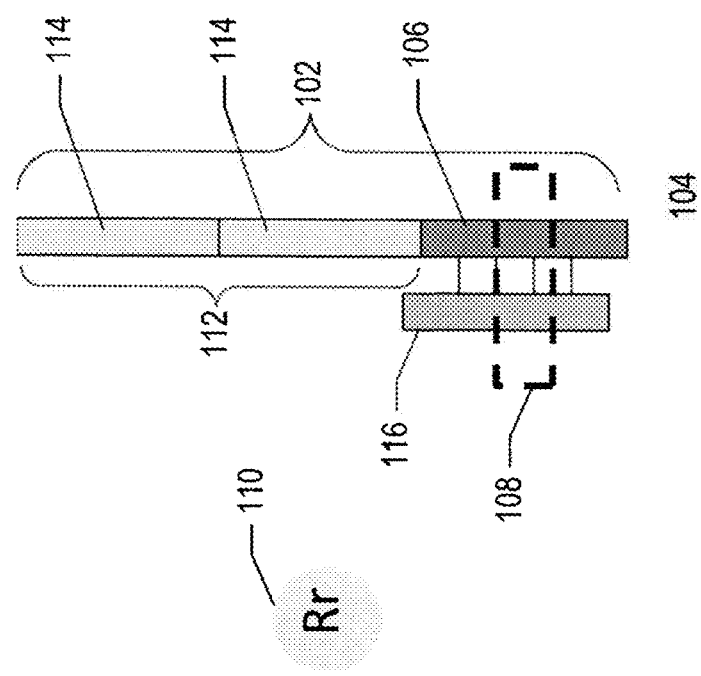
FIG. 1

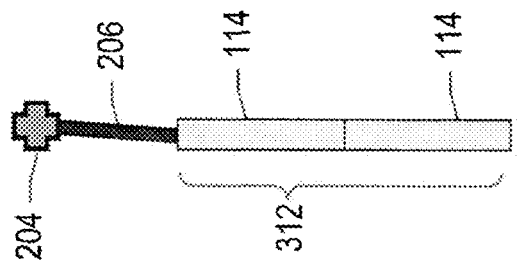
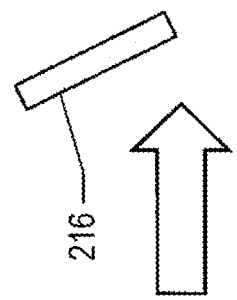
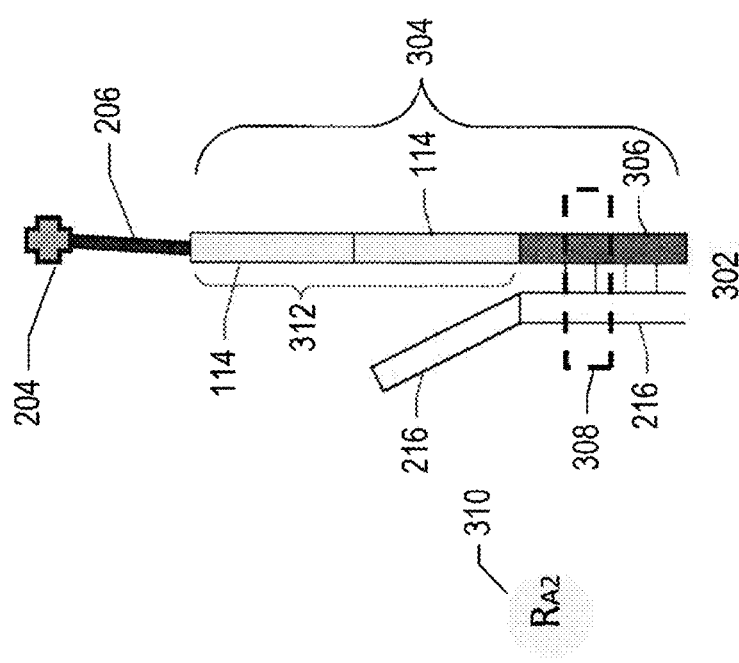
FIG. 3

Table 1

| Usage | Oligo name | Oligo sequence | 5' mod | REase | Length |
|---|---|---|---|---|---|
| primer | RV | CTATACAAGATATCTAACATC | no | EcoRV | 22 |
| primer | SP | GTCTAGTAATATTCTCAACA | no | SspI | 20 |
| primer | bi-pA-ARV(GT) | AAAAAAAAAAAAAGATGTTAGGATATCTTGTATAGGT | biotin | EcoRV | 36 |
| primer | bi-pA-ASP(CTAT) | AAAAAAAAAAAATGTTGAGAATATTACTAGACCTAT | biotin | SspI | 36 |
| primer | pC | CCCCCCTTTCCCCC | no | no | 14 |
| template | ARV-7SP-pG | GATGTTAGGATATCTTGTATAG 7x[GTCTAGTAATATTCTCAACA]GGGGGGGGGAAAGGGGGG | no | EcoRV, SspI | 180 |
| template | ASP-7RV-pG | TGTTGAGAATATTACTAGAC 7x[CTATACAAGATATCTAACATC]GGGGGGGGGAAAGGGGGG | no | SspI, EcoRV | 192 |
| target | AST | TCTTATAAGGCCTAACAAATAC | no | StuI | 22 |
| recognition probe | bi-pC-ST-SP | CCCCCCGTATTGTTAGGCCTTATAAGAGTCTAGTAATATTCTCAACA | biotin | StuI, SspI | 48 |
| HRP tag | ThiolpC | CCC CCCTTTCCCCCCCC | Thiol | none | 18 |

FIG. 8

METHODS AND SYSTEMS THAT DETECT NUCLEIC-ACID TARGETS

CROSS-REFERENCE TO RELATED APPLICATION

This application claims the benefit of Provisional Application No. 62/539,984, filed Aug. 1, 2017.

REFERENCE TO AN ELECTRONIC SEQUENCE LISTING

The contents of the electronic sequence listing (wordseqlist-1.txt; Size: 4 KB, and Date of Creation: Oct. 30, 2018) is herein incorporated by reference in its entirety.

TECHNICAL FIELD

The current document relates generally to the field of nucleic-acid detection and, in particular, to a highly sensitive and specific nucleic-acid-detection method that includes hybridization of a specific nucleic-acid target to a recognition probe, subsequent specific cleavage of the double-stranded target-probe helix at a specific restriction site, and exponential amplification of the enzymatic cleavage accompanied by release of a molecular marker.

BRIEF DESCRIPTION OF THE DRAWINGS

FIG. 1 shows the recognition state of the currently disclosed method.

FIG. 3 shows another portion of the amplification stage of the currently disclosed method.

FIG. 8 shows a table, Table 1, that provides a list of oligonucleotides used in experimental verification of methods and systems discussed with reference to FIGS. 1-6.

DETAIL DESCRIPTION

Figure 2:
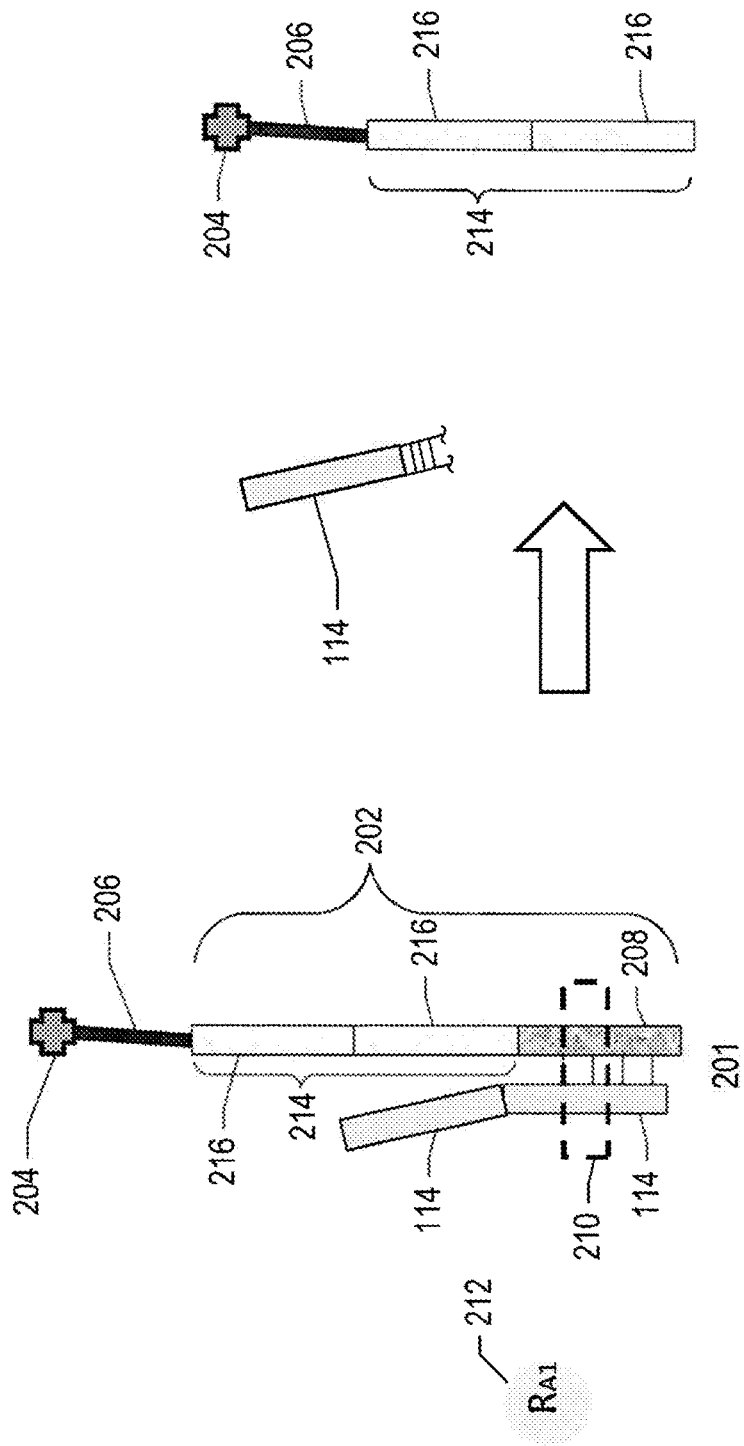
FIG. 2 shows a portion of the amplification stage of the currently disclosed method.

Currently Disclosed Methods and Systems for Nucleic-Acid Detection

The current document describes a highly sensitive and specific nucleic-acid detection method which includes: (1) hybridization of a specific nucleic-acid target to a recognition probe, an oligonucleotide immobilized on solid support; (2) subsequent specific cleavage of the double-stranded target-probe helix at a specific restriction site by a corresponding restriction endonuclease ("REase"); and (3) exponential amplification of the enzymatic cleavage accompanied by release of a molecular marker into a reaction solution. Nucleic acids include naturally occurring deoxyribonucleic acids and ribonucleic acids, but may also include various types of non-naturally-occurring nucleic acids, such as nucleic acids containing non-naturally-occurring pyrimidine and purine bases, sugars, and backbone moieties.

In certain implementations, the specific recognition probe is single-stranded and is designed to have a recognition part, or a segment of a first type, that is complementary to the target, and an amplification part, or amplification segment, that consists of two or more identical subsequences of a second subsequence type. In certain implementations, the recognition probe is bound to a solid support in a recognition-reaction chamber. The solid support may be nanoparticles, beads, a substrate, or immobile-phase components of a gel. The first-type segment, complementary to the target, is proximal to a first end of the recognition probe adjacent to the solid support and the two or more identical subsequences of the second subsequence type are adjacent to a second end of the recognition probe. The recognition probe can be denoted: "ss-$S_1$-$S_2$ ... $S_2$ where $S_1$|target." In this symbolic representation of the recognition probe, "ss" indicates the solid support, "$S_1$" indicates the segment of the first type, "$S_2$" indicates a segment of the second type, " ... " represents 0, 1, or more segments of the same type as the segments adjacent to " ... " in the symbolic representation, and "$S_1$|target" indicates that the segment of the first type, $S_1$, is complementary to the target.

In certain implementations, an amplification reaction chamber contains two different types of solid-support-bound single-stranded oligonucleotide amplification probes and corresponding REases, where, again, the solid support may be nanoparticles, beads, or a substrate, or immobile-phase components of a gel. In alternative implementations, there may be additional or fewer chambers.

In certain implementations, a first type of amplification probe includes a third type of subsequence proximal to a first end of the first-type amplification probe adjacent to the solid support and at least two subsequences of a fourth type proximal to a second end of the first-type amplification probe. The first type of amplification probe can be denoted, using the same representation conventions described above in the representation of the recognition probe: "ss-$S_3$-$S_4$ ... $S_4$ where $S_3$|$S_2$."

In certain implementations, a second type of amplification probe includes a fifth type of subsequence proximal to a first end of the second-type amplification probe adjacent to the solid support and at least two subsequences of the second type proximal to a second end of the second-type amplification probe. The second type of amplification probe can be denoted, using the same representation conventions described above in the representation of the recognition probe: "ss-$S_5$-$S_2$ ... $S_2$ where $S_5$|$S_4$."

The subsequence of the second type of the second type of amplification probe is complementary to the fourth type of subsequence of the first type of amplification probe and the third type of subsequence of the first type of amplification probe is complementary to the second type of subsequence of the recognition probe. The third type of subsequence of the first type of amplification probe and the fifth type of subsequence of the second type of amplification probe contain restriction sites specific for enzymatic cleavage by first and second types of amplification REases, respectively. Both types of amplification probes have a molecular marker attached to their second ends. The first type of subsequence of the recognition probe contains a restriction site specific for enzymatic cleavage by a recognition REase.

Upon recognition-REase cleavage of the recognition probe, the released second-type segments are transported into the amplification chamber, in certain implementations. There, a second-type segment released by recognition-REase cleavage of the recognition probe hybridizes with the third type of subsequence of the first type of amplification probe and the resultant double-stranded hybrid is cleaved the first type of amplification REase. This enzymatic cleavage of the first type of amplification probe leads to the release of multiple copies of the fourth type of subsequence of the first type of amplification probe and the molecular marker into the reaction solution. The released fourth-type segments then hybridize with fifth-type of subsequences of the second type of amplification probe. The hybrids are then cleaved by the second type of amplification REase. Each cleavage of the second type of amplification probe results in the release of multiple copies of the second type of sub-segment of the second type of amplification probe, also initially present in the recognition probe, and the molecular marker. In turn, each released second-type subsequence of the second type of amplification probe hybridizes with the third type of subsequence of the first type of amplification probe causing cleavage of the first type of amplification probe and release of multiple fourth-type subsequences of the first type of amplification probe and the molecular marker. Thus, enzymatic cleavage of the two types of amplification probes accelerates exponentially, resulting in an exponential increase in the concentration of free molecular marker in the reaction solution.

The currently disclosed method consists of two stages: (1) a recognition stage; and (2) an amplification stage. FIG. 1 shows the recognition stage of the currently disclosed method. A recognition probe 102 is immobilized on a solid surface 104. The recognition probe 102 is an oligonucleotide molecule that includes a recognition subsequence 106, or first type of subsequence, complementary to all or a portion of the target 116 and that contains a restriction site 108 specific for the recognition REase 110. The recognition subsequence 106 is attached to the solid support via either its 3' or 5' end. In other words, the recognition probe may have one of two possible orientations corresponding to 5'-to-3' and 3'-to-5', where 3' and 5' refer to hydroxy groups of the ribose subunits of the nucleotide monomers within the oligonucleotides. The recognition probe 102 additionally contains a subsequence 112 containing one or more copies of a second subsequence 114. The recognition stage involves hybridization of the target molecule 116 to subsequence 106 of the probe 102. The target molecule 116 is a single-stranded nucleic-acid molecule that carries at least one subsequence complementary to subsequence 106 of the recognition probe 102. Upon hybridization of the target 116 to the recognition probe 102, enzymatic cleavage of the target/restriction-probe duplex at the restriction site 108 by the recognition REase 110 occurs. This cleavage releases the one or more copies of the second subsequence 114 from the solid support into the reaction solution. Thus, following cleavage, the reaction solution contains oligonucleotide molecules 112 that each includes one or more copies of the second subsequence 114. The amount of released oligonucleotide molecules 112 is proportional to the amount of target molecules to which the recognition probes is exposed.

FIG. 2 shows a portion of the amplification stage of the currently disclosed method. The released oligonucleotide molecules 112 can either passively migrate or can be mechanically transported from a first reaction chamber, or recognition environment, to a second chamber, or amplification environment. In certain implementations, connected reaction chambers are employed, while in alternative implementations, probes that may deleteriously interact are spatially separated from one another in local environments, such as well-defined areas of a substrate or the surfaces of different beads or other different surfaces. The released oligonucleotide molecules 112 encounter a first type of amplification probe 202 that is bound, via a first end, to a solid support 201. A molecular marker 204 is attached to a second end of the first type of amplification probe 202 via a linker 206. The first type of amplification probe 202 is an oligonucleotide molecule that includes a third subsequence 208 complementary to the second subsequence 114 of the oligonucleotide molecules 112 released in the recognition stage. The third subsequence 208 contains a restriction site 210 specific for a first type of amplification REase 212. The first type of amplification probe 202 further includes a subsequence 214 that includes one or more copies of a fourth subsequence 216. Upon hybridization of an oligonucleotide molecule 112, through a component subsequence 114, to the first type of amplification probe 202, enzymatic cleavage of the released-oligonucleotide-molecule/first-type-amplification-probe duplex at the restriction site 210 by the first type of amplification REase 212 occurs. This cleavage leads to the release of subsequence 214 of the first type of amplification probe 202 as well as the attached molecular marker 204 from the solid support into the reaction solution. Thus, following enzymatic cleavage of the released-oligonucleotide-molecule/first-type-amplification-probe duplex, the reaction solution contains oligonucleotide molecules 214 that include the fourth type of subsequence 216. When the oligonucleotide molecules 214 include more than one copy of subsequence 216, the oligonucleotide molecules 214 again hybridize with another first-type amplification probe 202 via another subsequence 216. This hybridization again leads to an additional cleavage of a first-type amplification probe 202. Thus, the number of released oligonucleotide molecules 214 is proportional to the number of copies of subsequence 216 in the amplification chamber.

FIG. 3 shows another portion of the amplification stage of the currently disclosed method. The amplification chamber, or amplification environment, further contains a solid support 302 with an immobilized second type of amplification probe 304. The molecular marker 204 is attached to one end of the second-type amplification probe 304 via linker 206. The second-type amplification probe 304 is an oligonucleotide molecule that consists of a fifth type of subsequence which is complementary to the fourth type of subsequence 216. The fifth type of subsequence includes a restriction site 308 specific for a second type of amplification REase 310. The second-type amplification probe 304 additionally includes a subsequence 312 that includes one or more second-type subsequences 114. The oligonucleotide molecules 214 released from the first-type amplification probe passively migrate or are mechanically transported to the second-type amplification probe 304. Upon hybridization of the oligonucleotide molecules 214 via component subsequences 216 to the fifth type of subsequence 306 of the second-type amplification probe 304, enzymatic cleavage of the released-oligonucleotide-molecule/second-type-amplification-probe duplex at the restriction site 308 by the second type of amplification restriction REase 310 occurs. This cleavage leads to release of the subsequence 312 and the attached molecular marker 204 from the solid support into the reaction solution. Thus, following enzymatic cleavage of the of the released-oligonucleotide-molecule/second-typeamplification-probe duplex, the reaction solution contains contains oligonucleotide molecules that include one or more copies of the fourth type of subsequence 114. When the oligonucleotide molecules 214 contain more than one copy of the subsequence 216, the remaining portion of oligonucleotide molecules 214 again hybridize with another second-type amplification probe 304 via subsequence 216. This hybridization leads to additional cleavage of the second type of amplification probe 304. Thus, the number of released oligonucleotide molecules 312 is proportional to the number of oligonucleotide molecules 214 released during the first amplification stage described with reference to FIG. 2. The released oligonucleotide molecules 312 passively migrate, or are mechanically transported, back to the first type of amplification probe 202, hybridize with first type of amplification probe 202 via the second type of subsequence 208, and the hybridization and cleavage discussed with reference to FIG. 2 occurs again. During each subsequent cycle, additional molecular marker 204 is also released into the reaction solution together with oligonucleotide molecules 214 and 312. Upon completion of each cycle of oligonucleotide-molecule 312 release, the number of released oligonucleotide molecules 312 is equal to a×b, where a is the number of oligonucleotide molecules 214 released at the previous cycle and b is the number of fourth-type subsequences 216 in each oligonucleotide molecule 214. At the same time, upon completion of each cycle, the number of released oligonucleotide molecules 214 is equal to c×d, where c is the number of oligonucleotide molecules 312 released at the previous cycle and d is the number of second-type subsequences 114 in each oligonucleotide molecules 312. Thus, the reactions involving the oligonucleotide molecules 214 and 312 and the molecular marker 204 result in an exponential increase in the concentration of the molecular marker 204 in the reaction solution.

Figure 4:
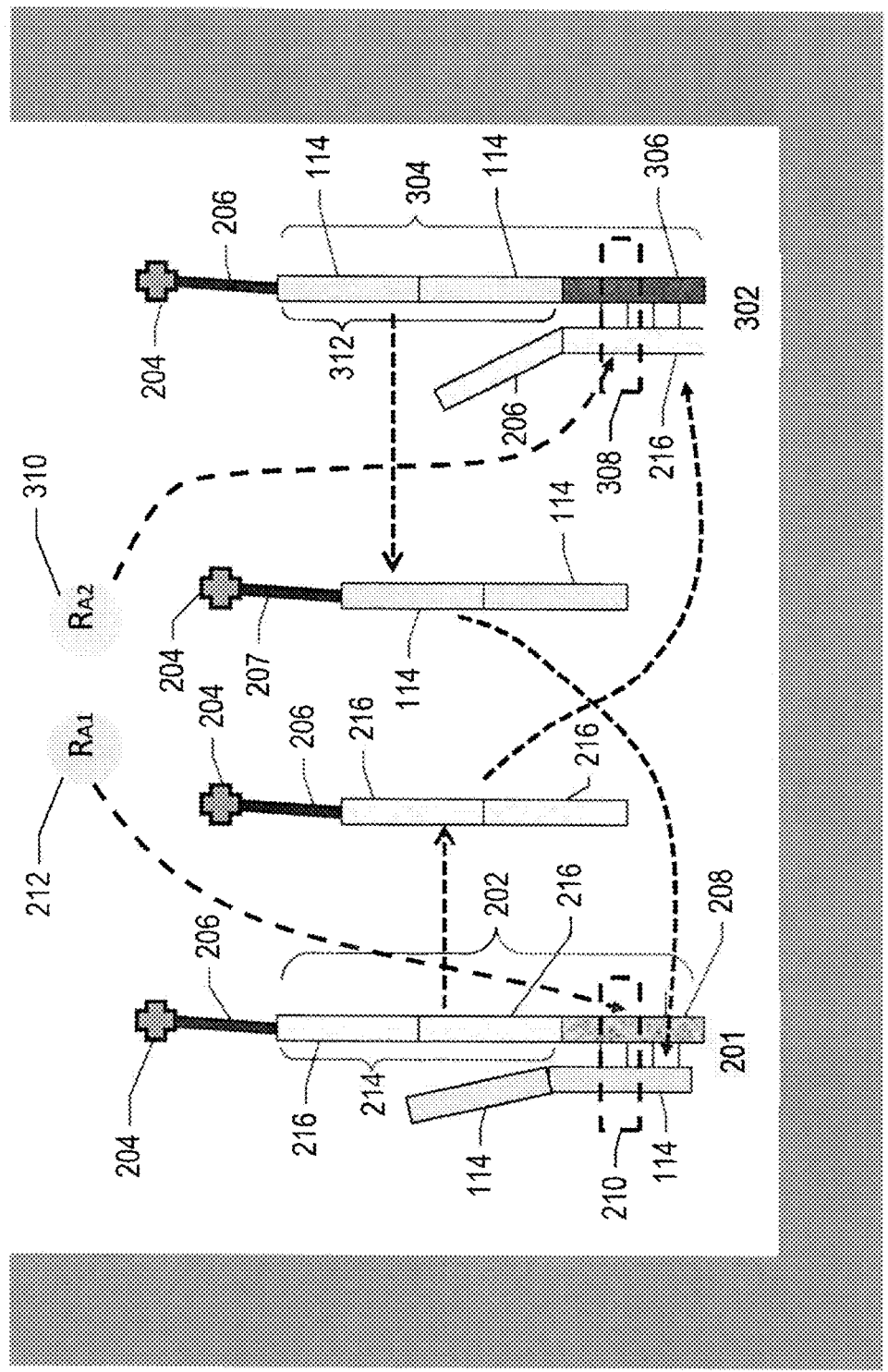
FIG. 4 shows the amplification chamber.

FIG. 4 shows one implementation of an amplification chamber. The amplification chamber is designed to provide separation of the first and second types of amplification probes 202 and 304 from the direct contact with each other. Thus, hybridization of the second-type subsequence 114 of the probe 304 with the third-type subsequence 208 of the first type of amplification probe 202 is impossible without the enzymatic cleavage and release of the oligonucleotide molecules 312. At the same time hybridization of the fourth-type subsequence 216 of the first type of amplification probe 202 with the fifth-type subsequence 306 of the second type of amplification probe 304 is impossible without the enzymatic cleavage and release of the oligonucleotide molecules 214. This separation is achieved by either physical separation of the solid supports 201 and 302 or localization of the first and second types of amplification probes 202 and 304 on a common solid support that does not permit physical contact between the two types of amplification probes.

After the enzymatic release of oligonucleotide molecule 312 by amplification REase 310 and oligonucleotide molecule 214 by amplification REase 212, the oligonucleotide molecules migrate to amplification probes 202 and 304, respectively. This migration results in hybridization of the second-type subsequence 114 with third-type subsequence 208 and hybridization of the fourth-type subsequence 216 with the fifth-type subsequence 306 followed by subsequent enzymatic cleavage of amplification probes 202 and 304. Since the oligonucleotide molecules 312 include two or more copies of the second-type subsequences 114, two or more enzymatic cleavages of the amplification probes 202 and 304 occur. Thus, each initial cleavage of the second-type amplification probe 304 is followed by two or more cleavages of the first-type amplification probe 202. This provides for a two-fold amplification of the signal per cycle. The initial cleavage of the first-type amplification probe 202 and the release of oligonucleotide molecules 214 provides for the signal amplification in a similar way. Since the oligonucleotide molecules 214 includes of two or more fourth-type subsequences 216, two or more enzymatic cleavages of the second-type amplification probe 304 occur after oligonucleotide molecules 214 migrate to the second-type amplification probe 304.

Figure 5:
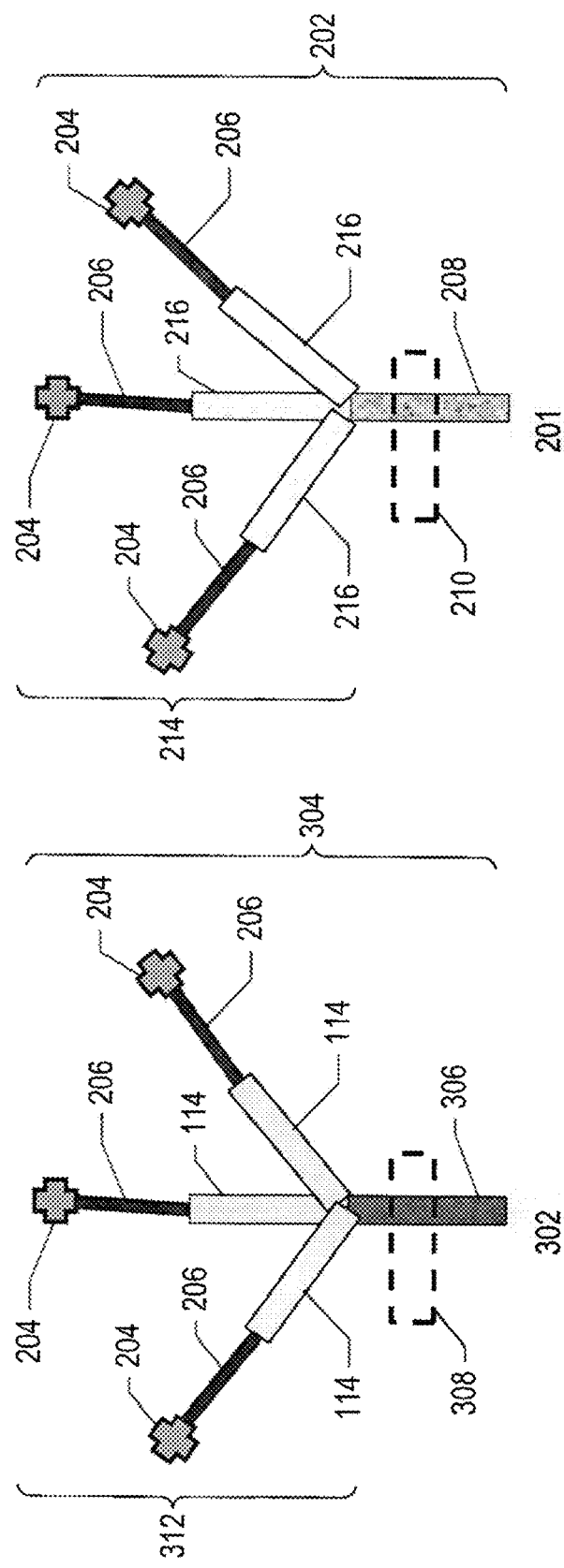
FIG. 5 shows the various alternative amplification probe designs.

FIG. 5 shows the various alternative amplification probe designs. The amplification probes 202 and 304 may be designed as linear molecules, as shown in FIGS. 2 and 3, but may alternatively be designed as branched molecules in which the multiple copies of the second-type subsequences 114 are linked to the fifth-type subsequence 306, forming oligonucleotide molecule 312 of the second-type amplification probe 304, and multiple fourth-type subsequences 216 are linked to third-type subsequence 208, forming oligonucleotide molecule 214 of the first-type amplification probe 202.

Figure 6:
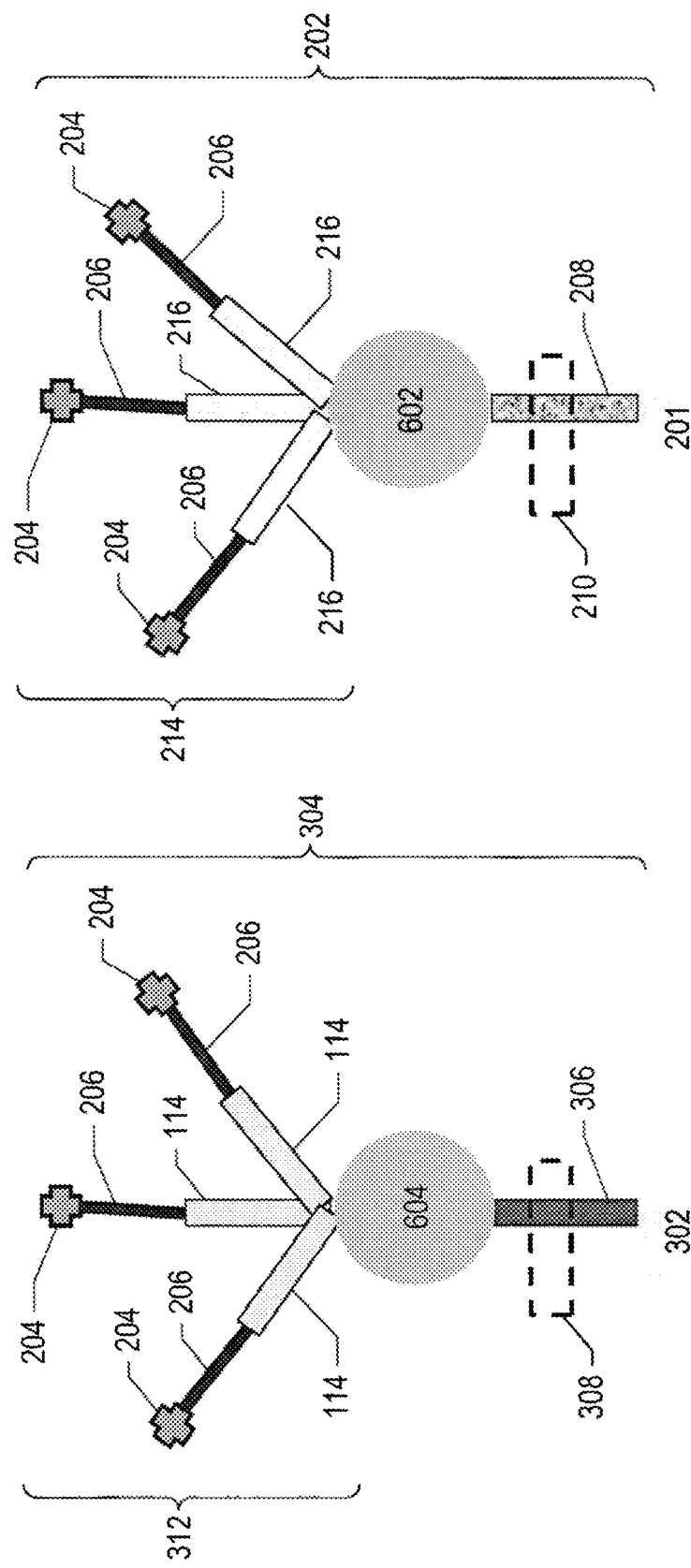
FIG. 6 shows an alternative amplification probe design.

FIG. 6 shows an additional alternative amplification probe design. The amplification probes 202 and 304 include carriers 602 and 604, respectively, linked to a third-type subsequence 208 and fifth-type subsequence 306. The carrier surface is modified with multiple fourth-type subsequences 216 and second-type segments 114, respectively, and with molecular markers 204. The carriers 602 and 604 can be particles of nano- and micro size, or protein, lipid, synthetic-polymer, and other types of macromolecules. Each carrier can contain a large number of fourth-type subsequences 216 and second-type segments 114, from hundreds to thousands or more, thus providing for high amplification coefficients.

The solid support for probe immobilization can be a solid, such as a metal or plastic, a gel, such as gelatin, alginate, etc., and various types of beads, micro-particles, nano-particles, and mixed-scale particles. An oligonucleotide probe can be linked to the gel via a biotin-streptavidin interaction, amino groups, sulfhydryl groups, aldehyde groups, etc.

The molecular marker can be one or more of: (1) a fluorescent label, such as fluorescein isothiocyanate, for fluorescent detection; (2) an enzyme label, such as horseradish peroxidase or alkaline phosphatase, to provide further enzymatic conversion of an enzymatic substrate for optical or electrochemical detection; and (3) an electrochemical label, such as ferrocene derivatives, to provide a substrate for electrochemical conversion and detection.

Figure 7:
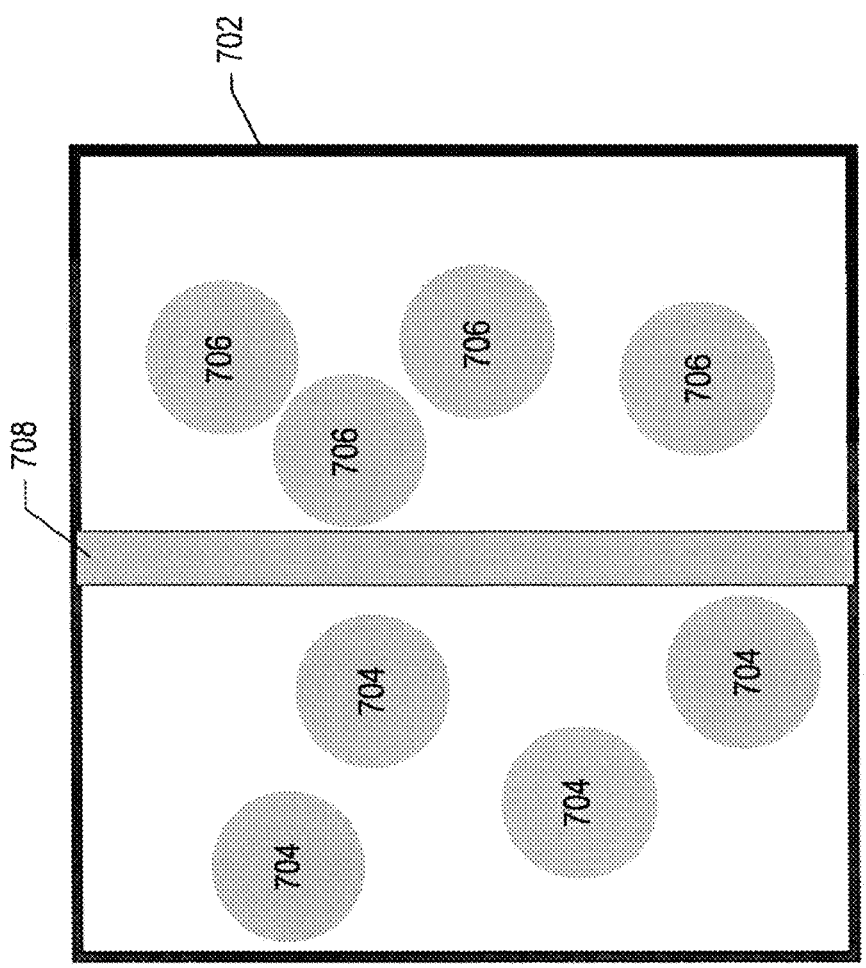
FIG. 7 illustrates one implementation for a DNA-detection

FIG. 7 illustrates one implementation of an amplification cell. The amplification cell 702 contains carriers 704 and 706 with amplification probes immobilized to their surfaces. The carriers 704 and 706 are separated by a barrier 708. The barrier 708 does not permit carriers 704 and 706 to interact with each other. At the same time the barrier 708 is permeable for all other participants of the amplification process: enzymes, oligonucleotides, ions, etc. The carriers are kept in suspended conditions during the amplification reaction by either alternating a magnetic field, by ultrasonic treatment, or by mechanical agitation.

Experimental Results

Oligonucleotide Probes for Recognition and Amplification

FIG. 8 shows a table, Table 1, that provides a list of oligonucleotides used in experimental verification of methods and systems discussed with reference to FIGS. 1-6. Table 1 provides a list of applied oligonucleotides purchased from Integrated DNA Technologies (Skokie, IL). The oligonucleotide bi-pC-ST-SP, with a biotinylated 5' end, was used as a probe for the recognition stage to detect the target AST. The oligonucleotides ARV-7SP-pG and ASP-7RV-pG were used as templates to generate biotinylated amplification probes using the polymerase chain reaction ("PCR"). Biotinylated oligonucleotides bi-pA-ARV(GT) and bi-pA-ASP(CTAT), and the biotin-free pC, were used as PCR primers. The thiol pC oligonucleotide was used to obtain an HRP linked tag for attachment of HRP to 3' ends of amplification probes.

HRP Conjugate Preparation

To attach the horseradish peroxidase ("HRP") marker to the amplification probes, HRP was conjugated to the oligonucleotide pC. The conjugation reaction was carried out with an excess of HRP compared to the oligonucleotide, producing a final conjugate concentration equivalent to the initial oligonucleotide pC concentration.

Amplification Probes Preparation Via PCR

The amplification probes were obtained by PCR using the Phusion® High-Fidelity PCR Kit (New England Biolabs, Ipswich, MA). The oligonucleotides ARV-7SP-pG and ASP-7RV-pG were used as templates at 1 nM concentrations. Primer pairs: bi-pA-ARV(GT) plus pC, and bi-pA-ASP(CTAT) plus pC were used for amplification of these templates, respectively.

PCR was performed under the following conditions: 10 sec at 95° C. denaturing, 20 sec at 58° C. annealing, and 20 sec at 72° C. extension, for 40 cycles. The PCR product was then purified by using the Invitrogen ChargeSwitch®-Pro PCR Cleaning Kit (Thermo Fisher Scientific Inc., Rockford, IL), and applied to a Micro Bio-Spin column with Bio-Gel P-6 ("P-6 column") (Bio-Rad, Hercules, CA) pre-equilibrated with phosphate buffered saline ("PBS"). The product volume was then adjusted to the initial PCR product volume before purification by adding PBS.

Note: Both biotinylated primers bi-pA-ARV(GT) and bi-pA-ASP(CTAT), and thus, the resultant amplification probes contain a spacer sequence of 12 adenines to increase the distance between the probe and the attachment surface (bead).

Amplification Probe Attachment to Magnetic Beads Surface

Figure 9:
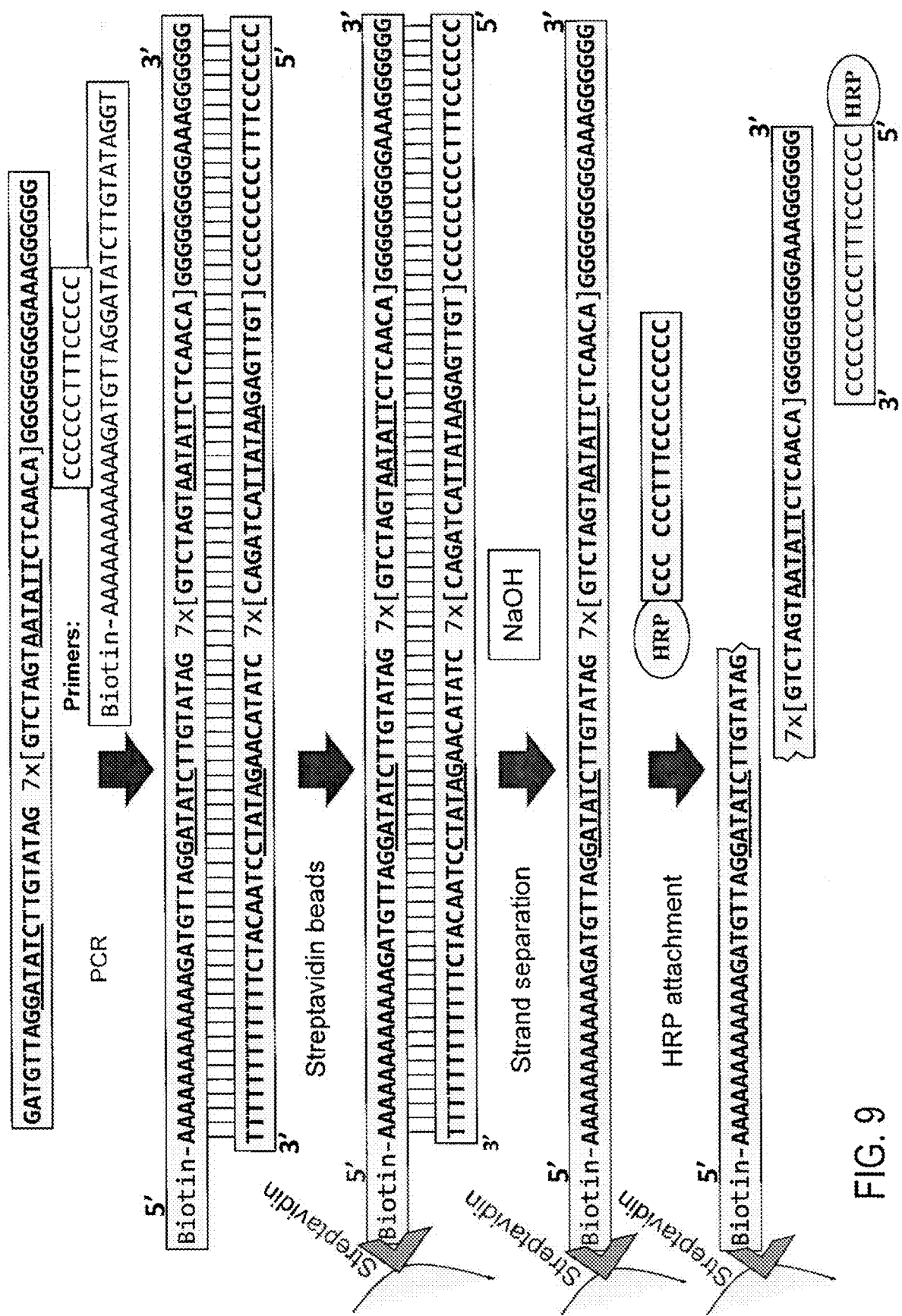
FIG. 9 shows a schematic of the process of amplification probe attachment to magnetic beads for the ARV(7SP)-pG probe.

Hydrophilic Streptavidin Magnetic Beads suspension (400 uL of 4 mg/mL stock, New England Biolabs) was settled and washed 2 times with 400 uL PBS. Then the beads were resuspended in 400 uL of 200 mM sodium hydroxide for 5 min to remove weakly bound streptavidin. The beads were then washed twice with 10×PBS and 3 times with 1×PBS. After drying, the beads were mixed with 400 uL of the purified PCR product (diluted 1:1 with PBS). The bead suspension was then incubated for 5 hours at room temperature in a Labquake Shaker Rotisserie (Thermo Fisher Scientific) set at 8 rpm. After incubation, the beads were washed 5 times with PBS and then treated with 400 uL of 200 mM sodium hydroxide for 5 min to denature double-stranded DNA. The beads were washed twice with 400 uL 10×PBS and 6 times with 1×PBS. Then the bead suspension was mixed with 800 uL PBS containing 150 nM HRP-pC conjugate and 0.5 mg/mL of BSA and incubated at room temperature overnight. Finally, the beads were washed 10 times with 800 uL of PBS and stored at 4° C. until use. The final working concentration of the beads in PBS was 2 mg/mL. FIG. 9 shows a schematic of the process of amplification probe attachment to magnetic beads for the ARV (7SP)-pG probe.

Amplification Test for Mixture of Beads with Two Different Amplification Probes 10 uL of beads (2 mg/mL) modified with either ASP-7RV-pG-HRP or ARV-7SP-pG-HRP were placed into separate 0.5 mL Eppendorf tubes. The beads were washed twice with 10 uL of CutSmart buffer (New England Biolabs, Ipswich, MA), and the supernatant was removed.

Next, 10 uL of CutSmart buffer containing a particular concentration of SP target oligonucleotide was added to the ASP-7RV-pG-HRP beads. The ARV-7SP-pG-HRP beads were used to add 10 uL of CutSmart buffer containing two REases, EcoRV and SspI (0.8 U/uL each). Finally, both bead suspensions were mixed together and incubated at 37° C. in a rotisserie. After incubation, the beads were settled, and the supernatant containing the cleaved HRP was collected for the signal measurement. The supernatant (18 uL) was placed into a microplate well and mixed with 100 uL of BioFX TMB One Component HRP Microwell Substrate (SurModics, Eden Prairie, MN) to start the HRP colored reaction. Negative controls (three) were prepared as no-target added samples. The blue color HRP-generated signal forming after 10-12 min incubation at room temperature was measured colorimetrically at the wavelength of 655 nM ($OD_{655}$) with a Bio-Rad iMark Microplate Reader.

Figure 10:
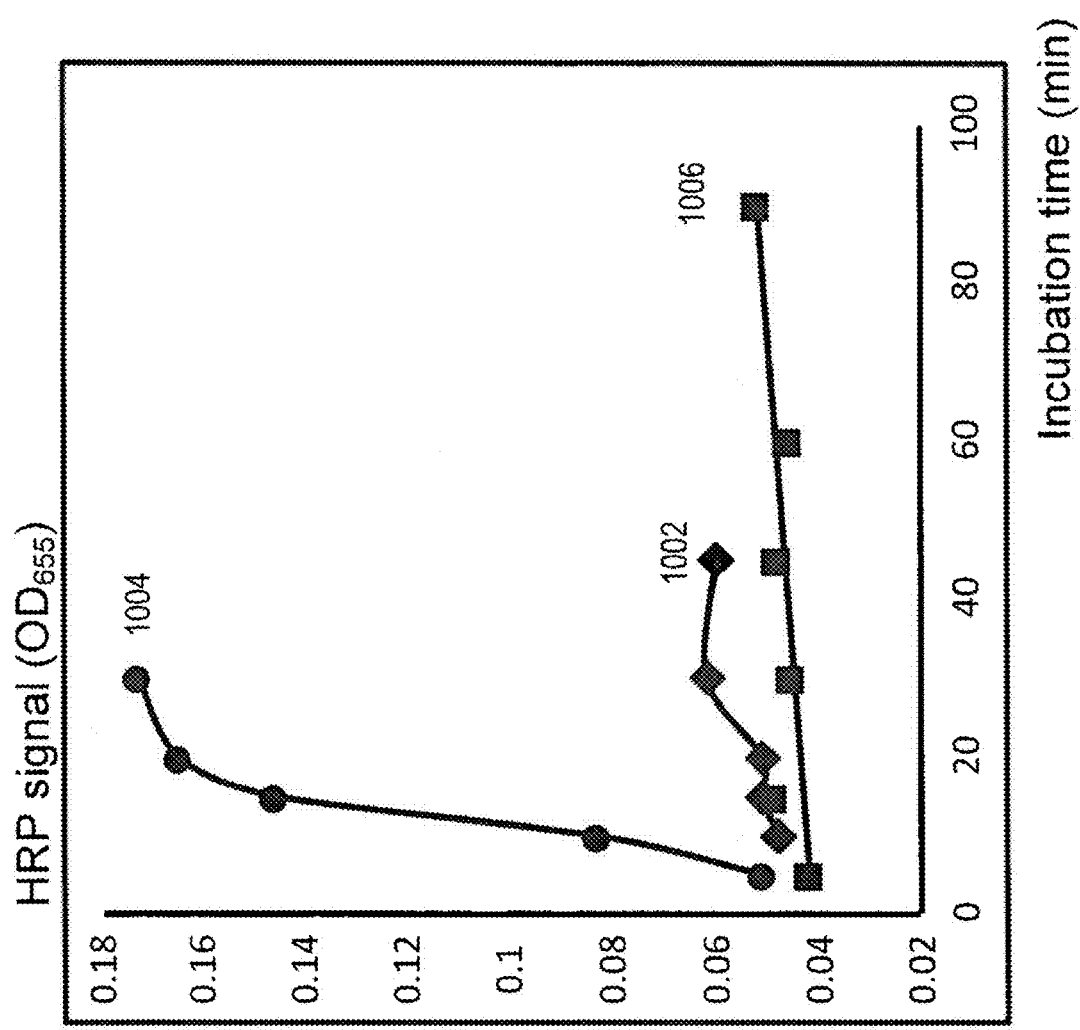
FIG. 10 shows the dependence of the HRP-generated signal on the incubation time for the two negative control samples.

FIG. 10 shows the dependence of the HRP-generated signal on the incubation time for the two negative control samples containing no-target added beads supplemented with either single SspI REase (1002 in FIG. 10), or both EcoRV and SspI REases (1004 in FIG. 10). Since both types of the beads are present in each suspension, the probes on the bead surfaces can hybridize to each other. Thus, the SP part of ARV-7SP-pG-HRP probe can hybridize to the ASP part of ASP-7RV-pG-HRP probe, and vice versa. Such hybridization of the SP and ASP complementary sequences is followed by the enzymatic cleavage of the probes by SspI enzyme. The cleavage releases the probes into the reaction solution, which can then be detected by measuring the HRP signal. FIG. 2 shows that, for the single REase system (1002 in FIG. 10), a slight increase of the HRP signal is observed after about 30 min incubation. For the two REase system (1004 in FIG. 10), a sharp increase of the signal is observed in the direct correlation with the incubation time increase. This prominent signal increase in the no-target added negative controls demonstrates that even very low level of random target-independent probe cleavage is triggering a cascade of exponential amplification reactions. A final curve 1006 shows that, when the two sets of beads are separated by a barrier, almost no increase in the HRP signal is observed.

Figure 11:
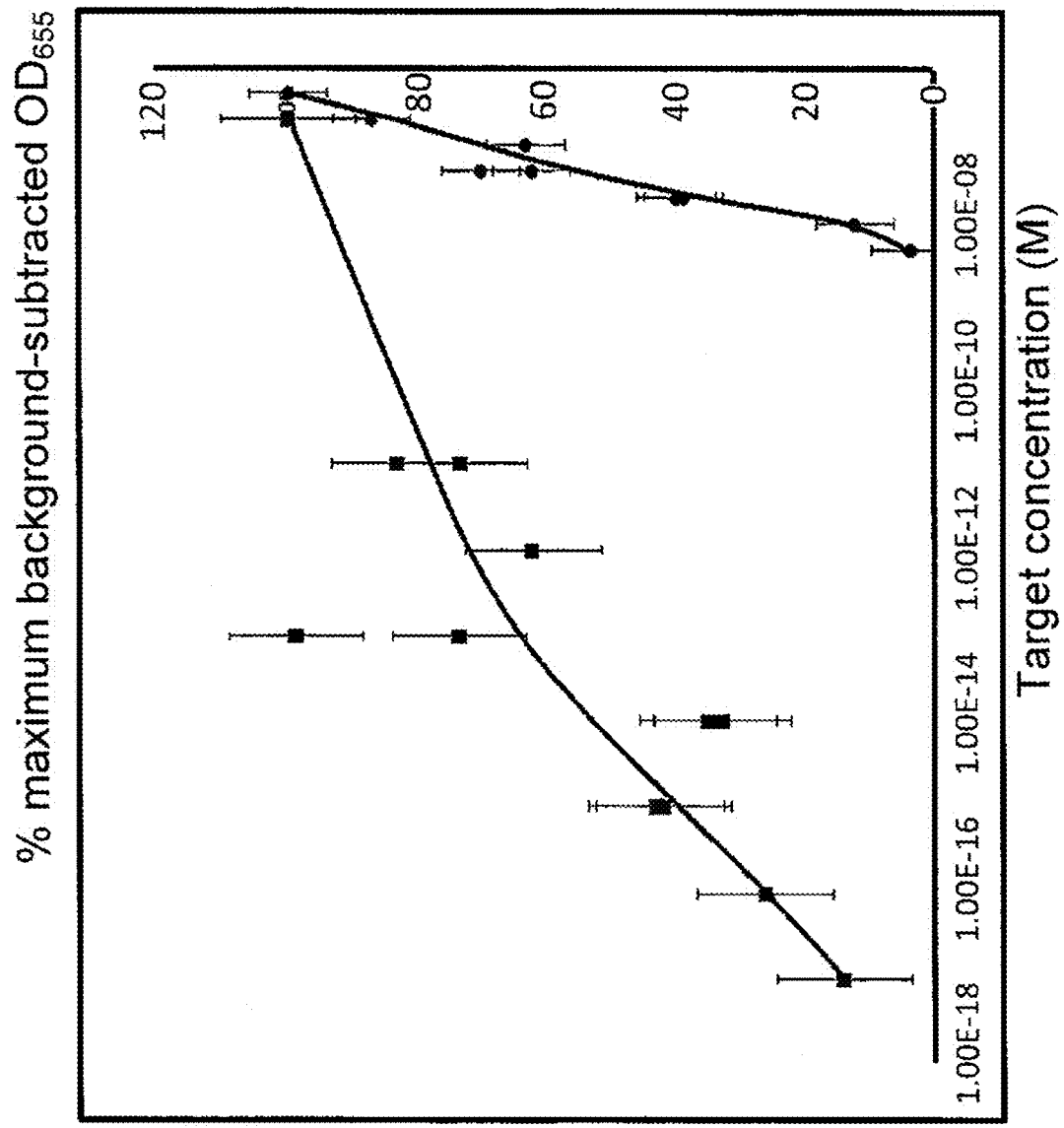
FIG. 11 shows the results of amplification target addition to the beads with immobilized probes after a 15-minute incubation time.

FIG. 11 shows the results of amplification-target ("SP") addition to the beads with immobilized probes after 15 min incubation time. The HRP signal was generated in either a single REase system (1102 in FIG. 11) or a two REase (EcoRV and SspI) (1104 in FIG. 11) system. The X-axis shows the target concentrations (M), and the Y-axis shows the background-subtracted HRP signal values, with the background calculated as the mean signal generated for triplicate no-target added negative controls. For normalization and comparison of the sample series, the HRP signal values are expressed as the percentages of the maximum background-subtracted $OD_{655}$ corresponding to each series. Error bars show standard deviations. FIG. 11 shows that, for the single-REase system (1102 in FIG. 11), the lower detection limit is in the nanomolar concentration range, which is expected, since it is incapable of signal amplification. The two REase system (1104 in FIG. 11) has a detection limit in the 10-100 attomolar range due to the exponential signal amplification.

Amplification Test for Barrier-Separated Beads with Two Different Amplification Probes To prevent formation of high negative control signals described above with reference to curve 1004 in FIG. 10), the amplification beads with probes ASP-7RV-pG-HRP and ARV-7SP-pG-HRP were separated with a physical barrier of glass filters permeable only to the soluble compounds. A 5-mm-diameter disk made of glass fiber of filter grade A (I.W. Tremont Co., Inc, Hawtrone, NJ) was placed into a microplate well. Next, 10 uL of ARV-7SP-pG-HRP modified bead suspension (2 mg/mL in CutSmart buffer) was deposited onto the filter. This was overlain with a second filter and topped with 10 uL of ASP-7RV-pG-HRP modified beads (2 mg/mL in CutSmart buffer). A magnetic field was then applied for 10 seconds to the bottom of the microplate to fix the beads on the top of filters. Next, 20 uL of the CutSmart buffer containing the SP target oligonucleotide was added to the well. Finally, 20 uL of CutSmart buffer containing two REases, EcoRV and SspI (0.8 U/uL each) was also added to the well. The resultant assembly microplate was then incubated for various time intervals at 37° C. with shaking at 90 revolutions per min. After incubation, 20 uL of PBS were added to the well and mixed with the reaction solution, and 50 uL of the mix was then collected. The residual beads were settled from the reaction mixture and 35 uL of the supernatant were placed into a microplate well and mixed with 150 uL of BioFX TMB One Component HRP Microwell Substrate to start the HRP colored reaction. The blue color HRP-generated signal that formed after 30-40 mM incubation at room temperature was measured colorimetrically at a wavelength of 655 nM ($OD_{655}$).

FIG. 10 shows the dependence of the HRP-generated signal on the incubation time for the negative control samples. These samples contain no-target added beads supplemented with both EcoRV and SspI REases (1006 in FIG. 10). Unlike the bead mixture (1002 in FIG. 10), the barrier-separated beads demonstrate almost no release of HRP even for a long incubation time of 90 min.

Figure 12:
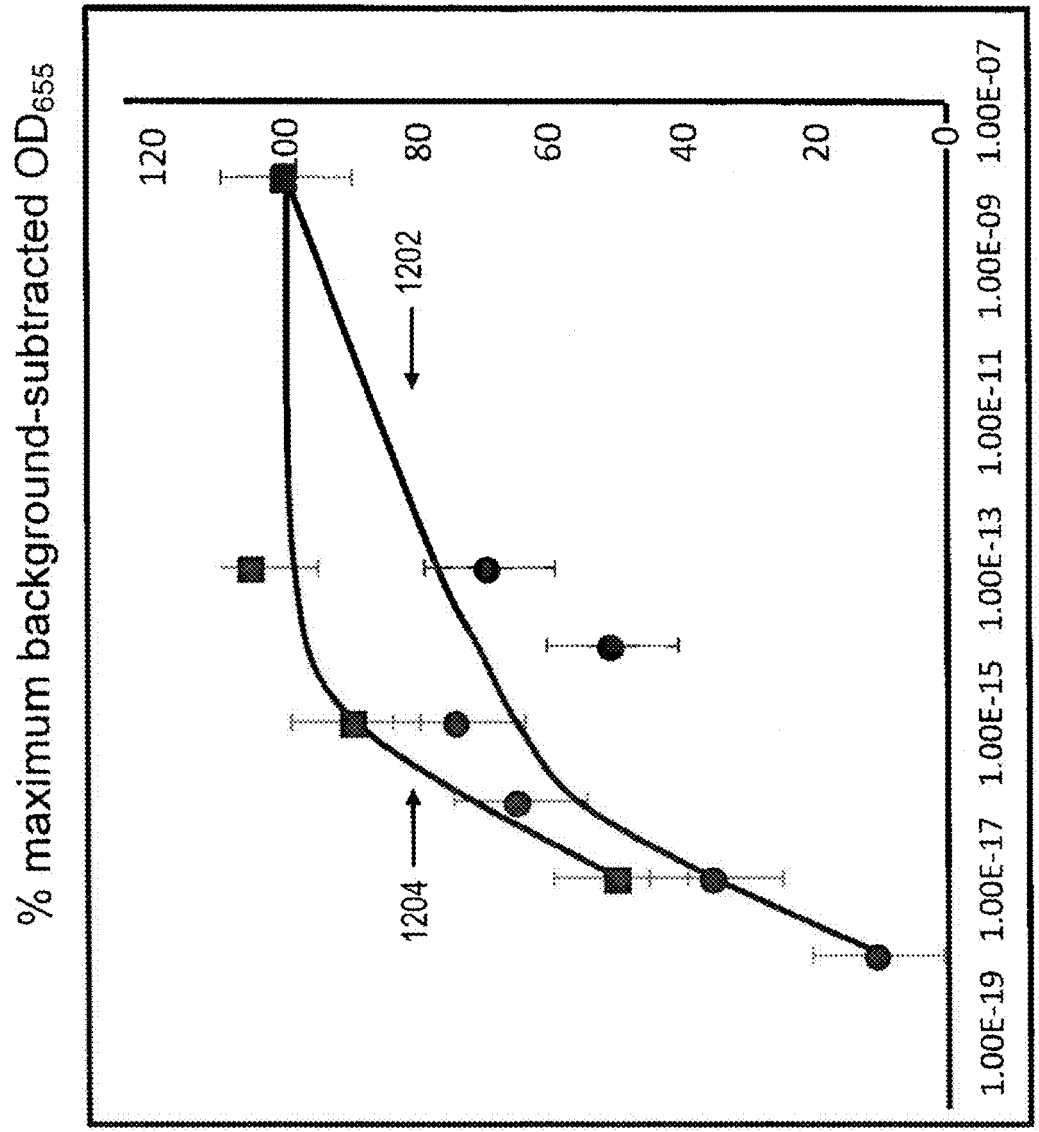
FIG. 12 shows the results of amplification target ("SP") addition to the barrier-separated beads.

FIG. 12 shows the results of amplification target ("SP") addition to the barrier-separated beads with immobilized probes after 80 min incubation time (1202 in FIG. 12). The HRP signal was generated in a two-REase (EcoRV and SspI) system. The X-axis shows the target concentrations (M) and the Y-axis shows the background-subtracted HRP signal values, with the background calculated as the mean signal generated for three replicates of no-target added negative controls. For normalization and comparison of the sample series, the HRP signal values are expressed as the percentages of the background-subtracted signal obtained at the highest concentration, 10 nM, corresponding to each series. Error bars show standard deviations. The two REase system with the barrier-separated beads (1202 in FIG. 12) has a detection limit in the 10 attomolar range due to the exponential signal amplification. However, the barriers separating the beads with different probes add diffusion limitations, requiring longer incubation times compared to the bead mixture-based system discussed with reference to FIG. 11. The overall HRP generated signal is also lower for the barrier-based system compared to the mixture-based one.

Recognition Probe Attachment to Magnetic Beads

A Hydrophilic Streptavidin Magnetic Bead suspension (200 uL of 4 mg/mL stock suspension) obtained from New England Biolabs (Ipswich, MA) was settled and washed 2 times with 200 uL PBS. The beads were then resuspended in 200 uL of 200 mM sodium hydroxide for 5 min to remove weakly bound streptavidin. The beads were then washed twice with 10×PBS and 3 times with 1×PBS. After removing the supernatant, the beads were mixed with 200 uL of the 1.6 nM solution of bi-pC-ST-SP oligonucleotide, the recognition probe, in PBS. The bead suspension was then incubated for 5 hours at room temperature in a Labquake Shaker Rotisserie (Thermo Fisher Scientific) at 8 rpm. After incubation, the beads were washed 5 times with PBS and then treated with 200 uL of 200 mM sodium hydroxide for 5 min to remove non-specifically and weakly bound probes. Finally, the beads were washed twice with 200 uL 10×PBS and 6 times with 1×PBS.

Combination of Recognition and Amplification Tests

The recognition beads were transferred to a saline-sodium-phosphate-EDTA ("SSPE") buffer to prepare a 2 mg/uL suspension. 10 uL of the bead suspension was then dried in a magnetic stand and supplemented with 40 uL of SSPE buffer containing the AST target. The reaction suspension was incubated for 40 min at ambient temperature in a rotisserie to achieve target-to-probe hybridization. The beads were then washed twice with SSPE buffer and 3 times with CutSmart buffer. Then, 20 uL solution of 0.2 U/uL of StuI REase was added and the beads were resuspended and incubated for 40 min at 37° C. in a rotisserie. After enzymatic cleavage of the pC-ST-SP probe, the supernatant containing the released SP oligonucleotide was collected and used for signal amplification, as described above in the section. The calibration curve obtained for AST target detection using the described procedure is shown in FIG. 12 (1204 in FIG. 12). This plot is similar to the plot generated using the amplification step only, also shown in FIG. 4 (1202 in FIG. 12). For both plots the detection limit is in the attomolar concentration range.

Although the invention has been explained in relation to its preferred embodiment, it is to be other possible modifications and variations can be made without departing from the spirit and scope of the invention. For example, as discussed above, many different types of apparatus may be used, various alternative apparatuses including one, two, or more interconnected reaction chambers, with solid-support-immobilized probes and cleavage products moved between chambers by mechanical solution transfer, applied magnetic fields, passive diffusion, and by other techniques. A single-chamber implementation is possible in addition to the barrier-implemented double chamber shown in FIG. 7. In additional implementations, a small fluid volume may be moved across a substrate, without the need for an enclosing chamber.

The invention claimed is:

1. A method that detects a nucleic-acid target molecule, the method comprising:
   in a first stage, introducing, to recognition probes,
      a sample solution containing the nucleic-acid target molecule, and
      recognition restriction endonucleases that cleave a target/recognition-probe duplex to produce a first nucleic-acid product;
   in a second stage, introducing, to amplification probes of two types, each bound to a solid support and each including a marker component, including a first-type amplification probe and a second-type amplification probe,
      the first nucleic-acid product, and
      two types of restriction endonuclease, including a second-type restriction endonuclease that cleaves a first-product/first-type-amplification-probe duplex and a third-product/first-type-amplification-probe duplex to produce a second nucleic-acid product and a third-type restriction endonuclease that cleaves a second-product/second-type-amplification-probe duplex to produce the third nucleic-acid product; and
   detecting marker component no longer bound to a solid support produced by multiple cycles of product production in the second stage.

2. The method of claim 1 wherein each recognition probe includes a first nucleic-acid subsequence complementary to at least a portion of the nucleic-acid target molecule and multiple copies of a second nucleic-acid subsequence.

3. The method of claim 2 wherein the target/recognition-probe duplex forms when the nucleic-acid target molecule associates with the complementary first nucleic-acid subsequence, to produce the first nucleic-acid product that includes multiple copies of the second nucleic-acid subsequence.

4. The method of claim 3 wherein the first-type amplification probe includes:
   a third nucleic-acid subsequence complementary to at least a portion of the second nucleic-acid subsequence; and
   multiple copies of a fourth nucleic-acid subsequence.

5. The method of claim 4 wherein the second-type amplification probe includes:
   a fifth nucleic-acid subsequence complementary to at least a portion of the fourth nucleic-acid subsequence; and
   multiple copies of the second nucleic-acid subsequence.

6. The method of claim 5
   wherein the first-product/first-type-amplification-probe duplex forms when the first nucleic-acid product associates with the complementary third nucleic-acid subsequence, to produce the second nucleic-acid product that includes multiple copies of the fourth nucleic-acid subsequence; and
   wherein the third-product/first-type-amplification-probe duplex forms when the third nucleic-acid product associates with the complementary third nucleic-acid subsequence, to produce the second nucleic-acid product that includes multiple copies of the fourth nucleic-acid subsequence.

7. The method of claim 6 wherein the second-product/second-type-amplification-probe duplex forms when the second nucleic-acid product associates with the complementary fifth nucleic-acid subsequence, to produce the third nucleic-acid product that includes multiple copies of the second nucleic-acid subsequence.

8. A system that detects a nucleic-acid target molecule, the system comprising:
   a first chamber that includes recognition probes, to which are introduced
      a sample solution containing the nucleic-acid target molecule, and
      recognition restriction endonucleases that cleave a target/recognition-probe duplex to produce a first nucleic-acid product;
   a second chamber that includes amplification probes of two types, each bound to a solid support and each including a marker component, including a first-type amplification probe and a second-type amplification probe, to which are introduced
      the first nucleic-acid product, and
      two types of restriction endonuclease, including a second-type restriction endonuclease that cleaves a first-product/first-type-amplification-probe duplex and a third-product/first-type-amplification-probe duplex to produce a second nucleic-acid product and a third-type restriction endonuclease that cleaves a second-product/second-type-amplification-probe duplex to produce the third nucleic-acid product.

9. The system of claim 8 wherein each recognition probe includes a first nucleic-acid subsequence complementary to at least a portion of the nucleic-acid target molecule and multiple copies of a second nucleic-acid subsequence.

10. The system of claim 9 wherein the target/recognition-probe duplex forms when the nucleic-acid target molecule associates with the complementary first nucleic-acid subsequence, to produce the first nucleic-acid product that includes multiple copies of the second nucleic-acid subsequence.

11. The system of claim 10 wherein the first-type amplification probe includes:
   a third nucleic-acid subsequence complementary to at least a portion of the second nucleic-acid subsequence; and
   multiple copies of a fourth nucleic-acid subsequence.

12. The system of claim 11 wherein the second-type amplification probe includes:
   a fifth nucleic-acid subsequence complementary to at least a portion of the fourth nucleic-acid subsequence; and
   multiple copies of the second nucleic-acid subsequence.

13. The system of claim 12
   wherein the first-product/first-type-amplification-probe duplex forms when the first nucleic-acid product associates with the complementary third nucleic-acid subsequence, to produce the second nucleic-acid product that includes multiple copies of the fourth nucleic-acid subsequence; and
   wherein the third-product/first-type-amplification-probe duplex forms when the third nucleic-acid product associates with the complementary third nucleic-acid subsequence, to produce the second nucleic-acid product that includes multiple copies of the fourth nucleic-acid subsequence.

14. The system of claim 13 wherein the second-product/second-type-amplification-probe duplex forms when the second nucleic-acid product associates with the complementary fifth nucleic-acid subsequence, to produce the third nucleic-acid product that includes multiple copies of the second nucleic-acid subsequence.

* * * * *

SEQUENCE LISTING

<160> NUMBER OF SEQ ID NOS: 11

<210> SEQ ID NO 1
<211> LENGTH: 22
<212> TYPE: DNA
<213> ORGANISM: Artificial Sequence

```
<220> FEATURE:
<223> OTHER INFORMATION: Purchased from Integrated DNA Technologies,
      Skokie, Illinois

<400> SEQUENCE: 1
ctatacaaga tatcctaaca tc                                                  22

<210> SEQ ID NO 2
<211> LENGTH: 20
<212> TYPE: DNA
<213> ORGANISM: Artificial Sequence
<220> FEATURE:
<223> OTHER INFORMATION: Purchased from Integrated DNA Technologies,
      Skokie, Illinois

<400> SEQUENCE: 2
gtctagtaat attctcaaca                                                     20

<210> SEQ ID NO 3
<211> LENGTH: 36
<212> TYPE: DNA
<213> ORGANISM: Artificial Sequence
<220> FEATURE:
<223> OTHER INFORMATION: Purchased from Integrated DNA Technologies,
      Skokie, Illinois

<400> SEQUENCE: 3
aaaaaaaaaa aagatgttag gatatcttgt ataggt                                   36

<210> SEQ ID NO 4
<211> LENGTH: 36
<212> TYPE: DNA
<213> ORGANISM: Artificial Sequence
<220> FEATURE:
<223> OTHER INFORMATION: Purchased from Integrated DNA Technologies,
      Skokie, Illinois

<400> SEQUENCE: 4
aaaaaaaaaa aatgttgaga atattactag acctat                                   36

<210> SEQ ID NO 5
<211> LENGTH: 14
<212> TYPE: DNA
<213> ORGANISM: Artificial Sequence
<220> FEATURE:
<223> OTHER INFORMATION: Purchased from Integrated DNA Technologies,
      Skokie, Illinois

<400> SEQUENCE: 5
ccccccttcc cccc                                                           14

<210> SEQ ID NO 6
<211> LENGTH: 180
<212> TYPE: DNA
<213> ORGANISM: Artificial Sequence
<220> FEATURE:
<223> OTHER INFORMATION: Purchased from Integrated DNA Technologies,
      Skokie, Illinois

<400> SEQUENCE: 6
gatgttagga tatcttgtat aggtctagta atattctcaa cagtctagta atattctcaa          60
cagtctagta atattctcaa cagtctagta atattctcaa cagtctagta atattctcaa         120
cagtctagta atattctcaa cagtctagta atattctcaa caggggggggg gaaagggggg        180

<210> SEQ ID NO 7
```

-continued

```
<211> LENGTH: 192
<212> TYPE: DNA
<213> ORGANISM: Artificial Sequence
<220> FEATURE:
<223> OTHER INFORMATION: Purchased from Integrated DNA Technologies,
      Skokie, Illinois

<400> SEQUENCE: 7
tgttgagaat attactagac ctatacaaga tatcctaaca tcctatacaa gatatcctaa      60
catcctatac aagatatcct aacatcctat acaagatatc ctaacatcct atacaagata    120
tcctaacatc ctatacaaga tatcctaaca tcctatacaa gatatcctaa catcggggg     180 gggaaagggg gg                                                        192

<210> SEQ ID NO 8
<211> LENGTH: 22
<212> TYPE: DNA
<213> ORGANISM: Artificial Sequence
<220> FEATURE:
<223> OTHER INFORMATION: Purchased from Integrated DNA Technologies,
      Skokie, Illinois

<400> SEQUENCE: 8
tcttataagg cctaacaaat ac                                              22

<210> SEQ ID NO 9
<211> LENGTH: 48
<212> TYPE: DNA
<213> ORGANISM: Artificial Sequence
<220> FEATURE:
<223> OTHER INFORMATION: Purchased from Integrated DNA Technologies,
      Skokie, Illinois

<400> SEQUENCE: 9 cccccccgtat ttgttaggcc ttataagagt ctagtaatat tctcaaca                 48

<210> SEQ ID NO 10
<211> LENGTH: 18
<212> TYPE: DNA
<213> ORGANISM: Artificial Sequence
<220> FEATURE:
<223> OTHER INFORMATION: Purchased from Integrated DNA Technologies,
      Skokie, Illinois

<400> SEQUENCE: 10 ccccccttc cccccccc                                                    18

<210> SEQ ID NO 11
<211> LENGTH: 192
<212> TYPE: DNA
<213> ORGANISM: Artificial Sequence
<220> FEATURE:
<223> OTHER INFORMATION: PCR product

<400> SEQUENCE: 11
aaaaaaaaaa aagatgttag gatatcttgt ataggtctag taatattctc aacagtctag      60
taatattctc aacagtctag taatattctc aacagtctag taatattctc aacagtctag    120
taatattctc aacagtctag taatattctc aacagtctag taatattctc aacagggggg    180
gggaaagggg gg                                                        192
```